US012799069B2

(12) United States Patent
Lu et al.

(10) Patent No.: US 12,799,069 B2
(45) Date of Patent: Nov. 17, 2026

(54) METHOD FOR PREPARING R-TERBUTALINE USING CHIRAL AUXILIARY GROUPS

(71) Applicant: SUZHOU HOMESUN PHARMACEUTICAL CO, LTD., Suzhou (CN)

(72) Inventors: Hongbin Lu, Suzhou (CN); Chao Fan, Suzhou (CN); Yingdong Yang, Suzhou (CN)

(73) Assignee: SUZHOU HOMESUN PHARMACEUTICAL CO, LTD., Suzhou (CN)

(*) Notice: Subject to any disclaimer, the term of this patent is extended or adjusted under 35 U.S.C. 154(b) by 591 days.

(21) Appl. No.: 18/282,913

(22) PCT Filed: Apr. 27, 2021

(86) PCT No.: PCT/CN2021/090369
§ 371 (c)(1),
(2) Date: Sep. 19, 2023

(87) PCT Pub. No.: WO2022/226812
PCT Pub. Date: Nov. 3, 2022

(65) Prior Publication Data
US 2024/0190807 A1 Jun. 13, 2024

(51) Int. Cl.
*C07C 217/70* (2006.01)
*C07C 213/00* (2006.01)
*C07C 313/06* (2006.01)

(52) U.S. Cl.
CPC .......... *C07C 217/70* (2013.01); *C07C 213/00* (2013.01); *C07C 313/06* (2013.01); *C07B 2200/09* (2013.01)

(58) Field of Classification Search
None
See application file for complete search history.

(56) References Cited

U.S. PATENT DOCUMENTS 5,442,118 A * 8/1995 Gao ...................... C07C 213/00
564/489

FOREIGN PATENT DOCUMENTS

CN 1273966 A 11/2000
CN 105330553 A 2/2016
(Continued)

OTHER PUBLICATIONS

Translation of Fan (CN110734382A, published on Jan. 31, 2020), obtained Apr. 2026. (Year: 2026).*
(Continued)

*Primary Examiner* — Amy C Bonaparte
(74) *Attorney, Agent, or Firm* — SZDC Law P.C.

(57) ABSTRACT

A method for preparing R-terbutaline by using a chiral auxiliary uses S-(−)-tert-butylsulfinamide as a starting material to sequentially react with tert-butylbromide and 1-(3,5-bis(benzyloxy)phenyl)-2-bromoethan-1-one to obtain a compound 5; the compound 5 is subjected to a reduction reaction under the catalysis of a quaternary ammonium salt to obtain a compound 6; the tert-butylsulfinyl group of compound 6 is deprotected to obtain a compound 7, and in the presence of a palladium catalyst and hydrochloric acid, the compound 7 is hydrogenolyzed in an alcohol solvent to obtain the R-terbutaline. The method is simple and reliable, the preparation costs are low, and the ee of the chiral product is as high as 99.9%.

7 Claims, 5 Drawing Sheets

(56) References Cited

FOREIGN PATENT DOCUMENTS

| | | | | | |
|---|---|---|---|---|---|
| CN | 106631831 A | | 5/2017 | | |
| CN | 108129367 A | | 6/2018 | | |
| CN | 110156614 A | * | 8/2019 | ........... | A61K 31/137 |
| CN | 110734382 A | * | 1/2020 | ........... | C07C 213/02 |

OTHER PUBLICATIONS

Translation of Lu (CN110156614AA, published on Aug. 23, 2019), obtained Apr. 2026 (Year: 2026).*
Liao Jian et al., "Facile resolution of racemic terbutaline and a study of molecular recognition through chiral supramolecules based on enantiodifferentiating self-assembly" Org. Biomol. Chem. No. 1 pp. 1080-1085 (Feb. 20, 2003).
Uchimoto Hitomi et al., "Green Synthesis of (R)-Terbutaline for Recyclable Catalytic Asymmetric Transfer Hydrogenation in Ionic Liquids" Chemical and Pharmaceutical Bulletin, vol. 65, Nr.: 4, pp. 389-395 (Dec. 31, 2017).

* cited by examiner

*FIG.*3

<Chromatogram>

<Peak Table>

PDA Ch1 254nm

| Peak# | Ret. Time | Area | Height | Conc. | Unit | Mark | Name |
|---|---|---|---|---|---|---|---|
| 1 | 12.677 | 2322361 | 65813 | 100.000 | % | | RT:12.677 |
| Total | | 2322361 | 65813 | | | | |

<Chromatogram>

<Peak Table>

PDA Ch1 254nm

| Peak# | Ret. Time | Area | Height | Conc. | Unit | Mark | Name |
|---|---|---|---|---|---|---|---|
| 1 | 13.654 | 3541985 | 96971 | 46.877 | % | | RT:13.654 |
| 2 | 18.423 | 4013872 | 81475 | 53.123 | % | M | RT:18.423 |
| Total | | 7555857 | 178445 | | | | |

METHOD FOR PREPARING R-TERBUTALINE USING CHIRAL AUXILIARY GROUPS

This application is the National Stage Application of PCT/CN2021/090369, filed on Apr. 27, 2021, which is incorporated by reference for all purposes as if fully set forth herein.

TECHNICAL FIELD

The present invention belongs to the field of pharmaceutical technology, and specifically relates to a chiral method for preparing R-terbutaline.

BACKGROUND OF INVENTION

Terbutaline is a rapid-acting and short-acting β-adrenal receptor agonist, which selectively agonizes β2 receptors, relaxes bronchial smooth muscle, inhibits the release of endogenous spasmolytics, and suppresses edema caused by increased clearance of endogenous transmitters and mucosal cilia (Kyeong H. K., Hyun J. K., Seon-Pyo H., Sang D. S., Arch. Pharm. Res. 2000,23:441-445). It is mainly clinically used to treat bronchial asthma, asthmatic bronchitis, emphysema, and bronchospasm in chronic obstructive pulmonary disease. Terbutaline has a chiral center of benzylic secondary alcohols, but currently, racemates are used in clinical practice. Research has shown that the levoisomer of terbutaline is the effective ingredient for its efficacy (*J. Med. Chem.,* 1972, 15, 1182-1183). The dextroisomer is not only ineffective, but also has toxic side effects. Therefore, studying the preparation method for R-terbutaline and re-marketing this levoisomer has important clinical application value. For example, CN110156614A has disclosed that R(−)terbutaline can significantly increase its anti-asthma efficacy compared to commercially available racemates, providing a new preferred treatment option for asthma related diseases.

The preparation methods for R-terbutaline that have been disclosed mainly include the following:

1. Separation method. The use of tartaric acid or tartaric acid derivatives for the separation of racemic Terbutaline is the simplest and most intuitive method for preparing R-terbutaline (CN1273966A, CN201810147612.1). However, this method often requires multiple crystallizations to obtain satisfactory enantiomeric purity, the whole process is complicated, the yield is low, and at least half of the product is discarded, which is not in line with the principle of green chemistry currently advocated.
2. Enzymatic method. Enzyme reduction method is a commonly used method for preparing chiral secondary alcohols from prochiral ketones, but it requires screening suitable enzyme catalysts and often has disadvantages such as low reduction efficiency (Journal of Molecular Catalysis B: Enzymatic, 84, (2012), 83-88).
3. The reduction of prochiral ketones by borane under the action of chiral boron catalysts (Corey-Bakshi-Shibata catalysts or similar) has the disadvantages of borane toxicity and difficulty in post-treatment, making it difficult to achieve industrial production.
4. The asymmetric reduction of 2-chloroacetophenone is achieved through chiral ruthenium-catalyzed transfer hydrogenation to obtain the key intermediate for the synthesis of R-terbutaline (Chem. Pharm. Bull. 65, (2017), 389-395). This type of method uses expensive precious metals, and the ee of the product is only 91%, which cannot meet the demand.

The existing technology has various disadvantages, so it is of great significance to develop a new method that is simple, efficient, and low-cost to prepare R-terbutaline.

TECHNICAL PROBLEMS

The purpose of the present invention is to provide a method for preparing R-terbutaline; and this method is simple and reliable, with low preparation cost, and the ee of chiral products is as high as 99.9%.

TECHNICAL SOLUTION

The technical solution of the present invention is: a method for preparing R-terbutaline using chiral auxiliary, wherein compound 7 is hydrogenated in an alcohol solvent in the presence of palladium catalyst and hydrochloric acid to obtain R-terbutaline; The chemical structural formula of compound 7 is as follows:

7

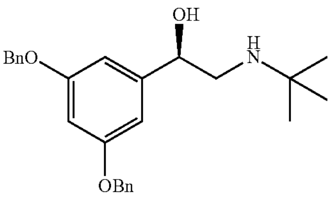

The chemical structural formula of R-terbutaline is as follows:

8

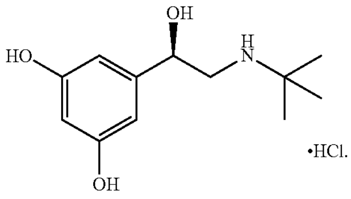

•HCl.

In the above technical solution, the palladium catalyst is a palladium carbon catalyst; The alcohol solvent is a small molecule alcohol, preferably methanol. Specifically, compound 7 is dissolved in methanol, a palladium carbon catalyst is added, hydrochloric acid is dropped dropwise, and hydrogenolysis is carried out in atmospheric hydrogen gas for 1-3 hours. The palladium carbon is removed by filtration, and the filtrate is distilled under reduced pressure, and the remaining solid is crystallized to obtain the product R-terbutaline hydrochloride.

In the present invention, S-(−)-tert-butylsulfinamide is used as the starting material to react with tert-butyl bromide and 1-(3,5-bis(benzyloxy)phenyl)-2-bromoethan-1-one sequentially to obtain compound 5; compound 5 underwent a reduction reaction to obtain compound 6; compound 6 is de-protected from tert-butylsulfonyl group to obtain Intermediate 7. The specific steps and compound structural formula are as follows:

(1) Preparation of tert-butyl sulfinylamide substituted acetophenone intermediate (compound 5). S-(−)-tert-butylsulfinamide 1 is dissolved in an organic solvent, a base is added, then tert-butyl bromide is added dropwise, and the reaction is carried out at 0-6 °C for 2-5 hours, followed by the addition of 1-(3,5-bis(benzyloxy)phenyl)-2-bromoethan-1-one 4, and the reaction is continued at 30-80 °C for 2-8 hours; at the end of the reaction, the solids are removed by filtration and then the solvent is removed by distillation under reduced pressure to obtain the compound 5, which is used directly for the next step of the reaction; and the anorganic solvent is acetonitrile, THF, DMF, acetone, toluene or ethyl acetate, preferably acetonitrile, THF and DMF, more preferably acetonitrile; and the bases are potassium carbonate, sodium carbonate, sodium hydroxide, potassium hydroxide, potassium phosphate, potassium fluoride, sodium hydride or potassium tert-butoxide, preferably potassium carbonate and sodium carbonate, more preferably potassium carbonate; the reaction is schematically shown below:

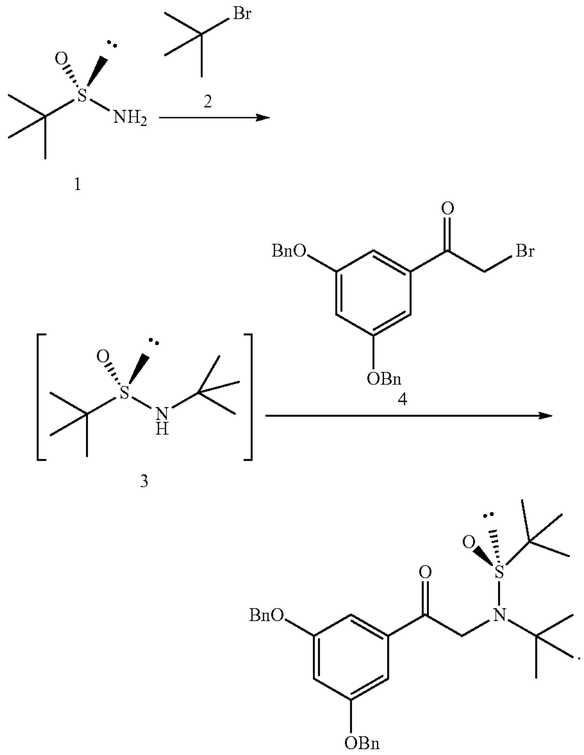

1 2 3 4 5

(2) The ketone is reduced to a chiral alcohol (compound 6) under the control of chiral tert-butyl sulfinamide. Compound 5 is dissolved in a solvent, quaternary ammonium salt is added, then sodium borohydride is added in batches over a period of 1-2 hours at 0-10 °C, stirring is continued for 1 hour after addition, then quenched by addition of aqueous ammonium chloride, extracted, dried, distilled under reduced pressure, and the residual solids are crystallized from ethanol to obtain compound 6; the organic solvent is one or several of THE, ethanol, methanol, isopropanol, preferably a mixture of THF and isopropanol; the quaternary ammonium salts are tetrabutylammonium bromide, tetrabutylammonium chloride, tetrapropylammonium bromide, tetraethylammonium bromide or triethylbenzylammonium bromide, preferably tetrabutylammonium bromide and tetrabutylammonium chloride, and more preferably tetrabutylammonium bromide; the reaction is illustrated below:

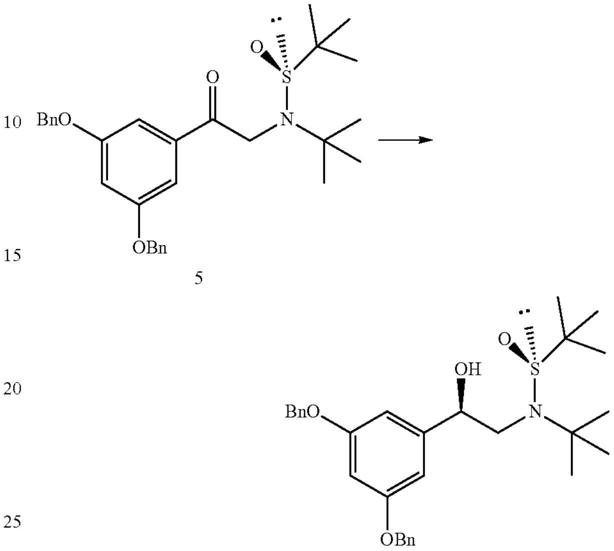

5

6

(3) The intermediate (compound 7) is obtained by deprotection of tert-butylsulfinyl group. The compound 6 is dissolved in methanol, and concentrated hydrochloric acid is added, and the reaction is carried out for 2~5 hours at 0~60 °C, and the solvent is removed by distillation under reduced pressure, and the residue is added with saturated solution of sodium bicarbonate, extracted with organic solvents, dried and distilled under reduced pressure to obtain the compound 7, which is directly used in the next step of the reaction. The reaction is illustrated below:

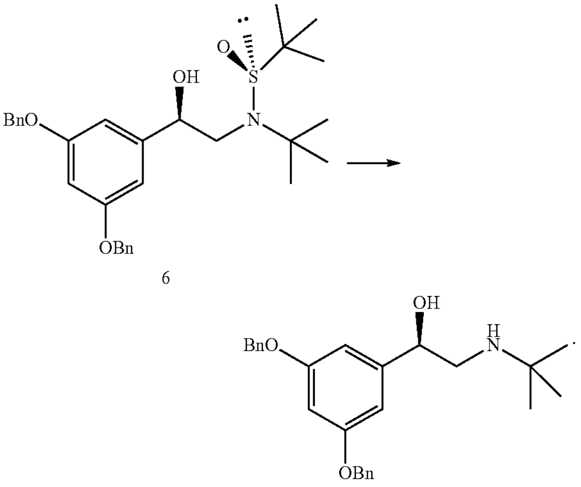

6

7

(4) The target product of R-terbutaline is obtained by deprotection of benzyl. The compound 7 is dissolved in methanol, a palladium carbon catalyst is added, hydrochloric acid is dropped dropwise, and hydrogenolysis is carried out in atmospheric hydrogen gas for 1-3 hours. The palladium carbon is removed by filtration, and the filtrate is distilled under reduced pressure, and the remaining solid is crystallized to obtain the R-terbutaline hydrochloride. The reaction is illustrated below:

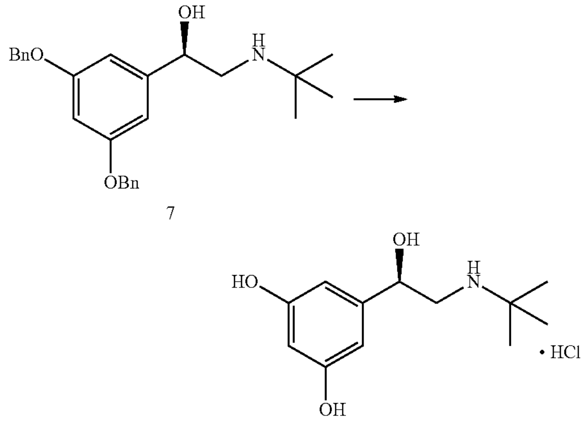

7

8

BENEFICIAL EFFECTS

Due to the use of the above technical solutions, the present invention has the following advantages over the prior art: The present invention uses for the first time a commercial and inexpensive chiral source of tert-butyl sulfinamide as a cofactor to control the asymmetric reduction of the ketone, and a small amount of the diastereoisomer is easily removed by crystallization, with an ee of the product as high as 99.9%; and the whole route is very simple to operate, and the reagents used are cheap, easy to obtain, non-toxic, so it's very suitable for industrialized production.

EXAMPLES OF THE PRESENT INVENTION

Figure 1:
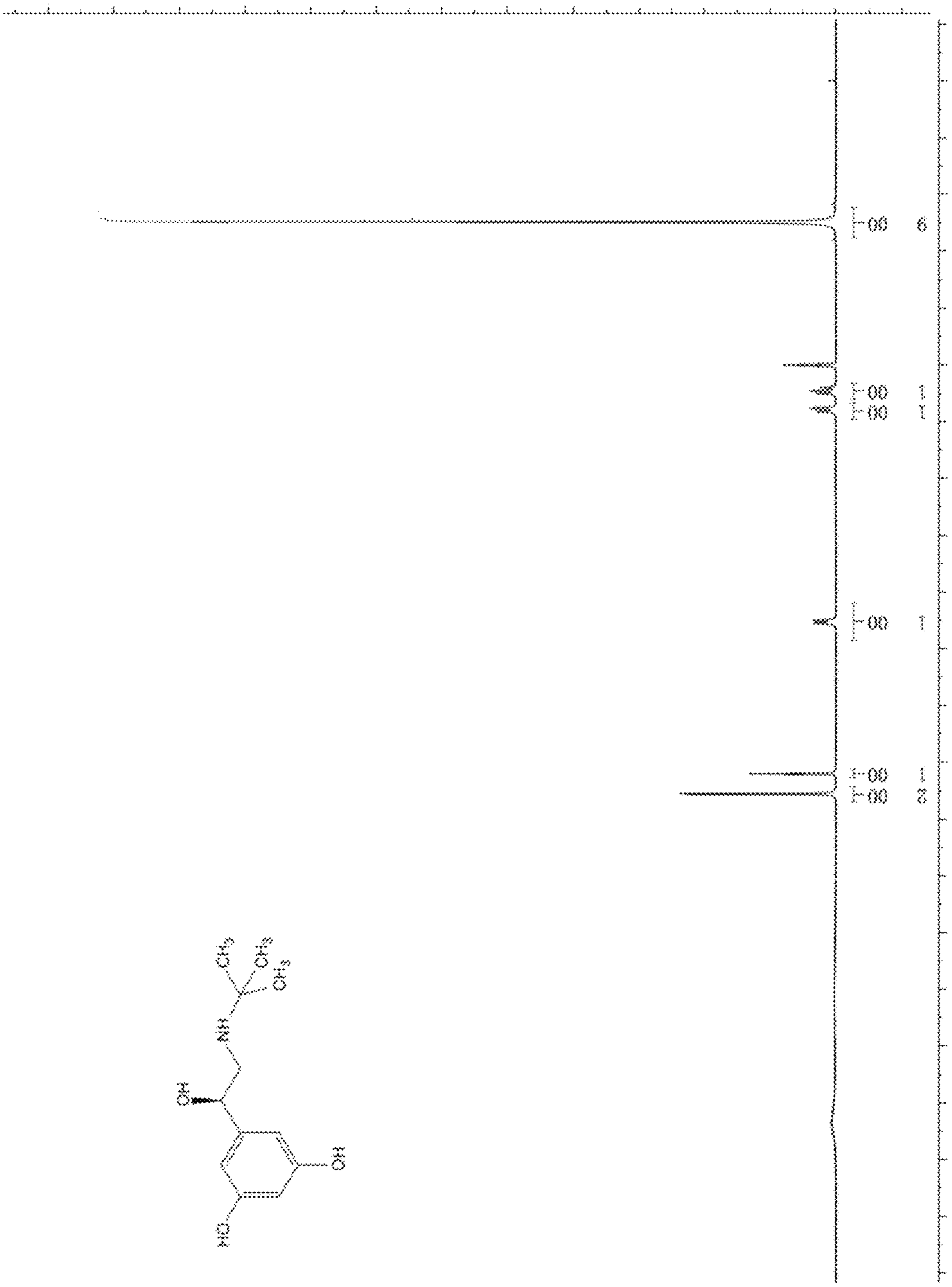
FIG. 1 shows the NMR hydrogen spectrum of the R-terbutaline hydrochloride prepared in the Example 1.
Figure 2:
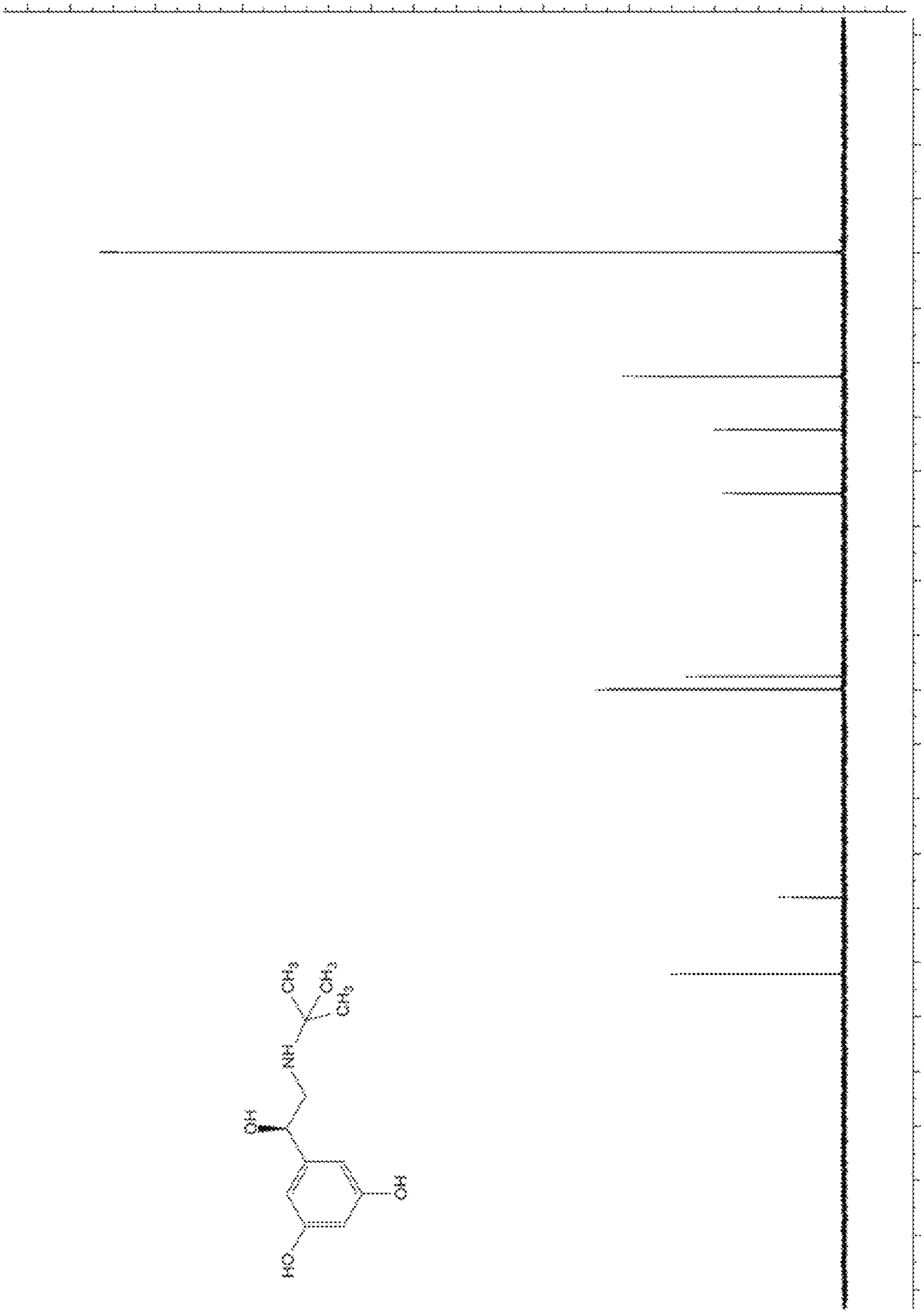
FIG. 2 shows the NMR carbon spectrum of the R-terbutaline hydrochloride prepared in the Example 1.
Figure 3:
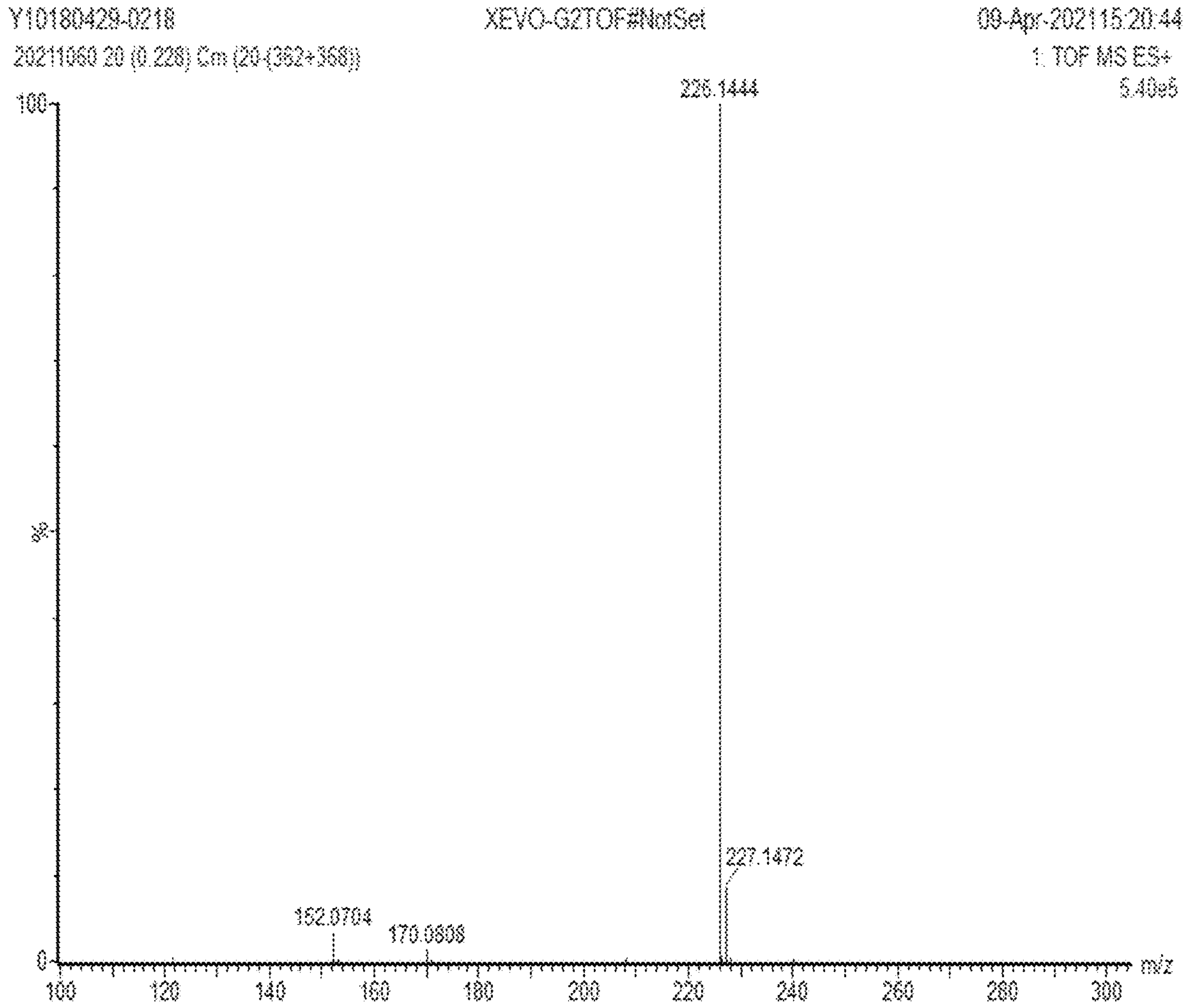
FIG. 3 shows the mass spectrum of the R-terbutaline hydrochloride prepared in the Example 1.
Figure 4:
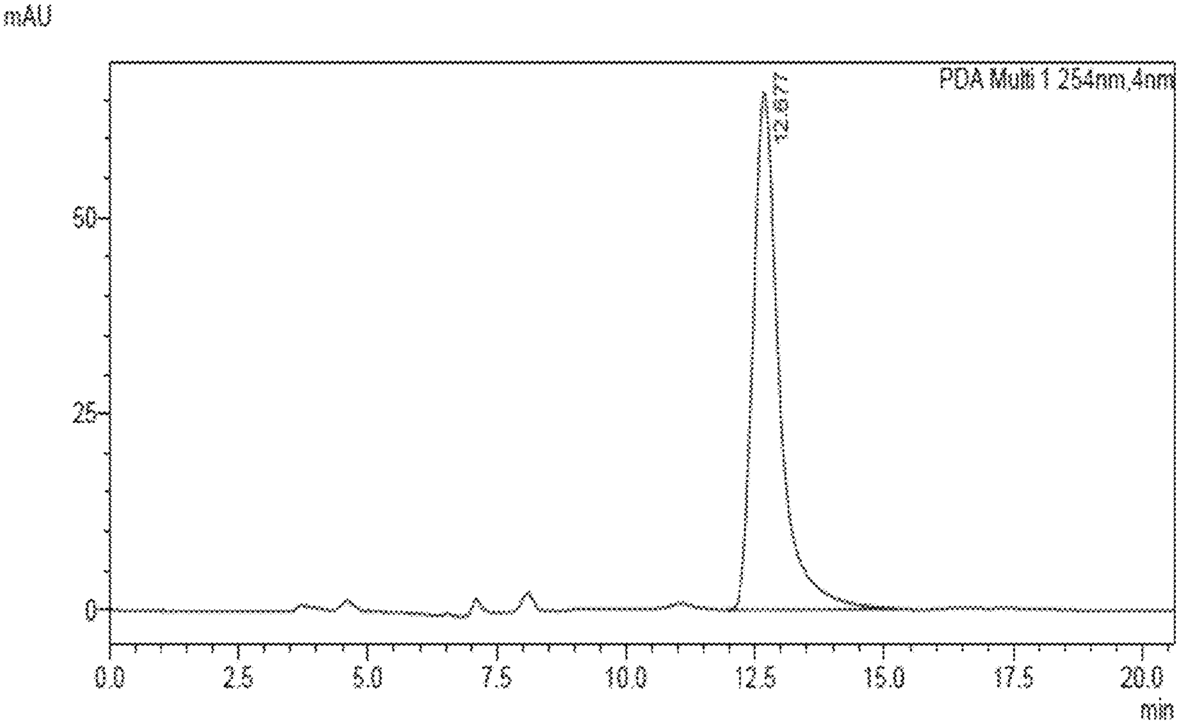
FIG. 4 shows the liquid chromatogram of the R-terbutaline hydrochloride prepared in the Example 1.
Figure 5:
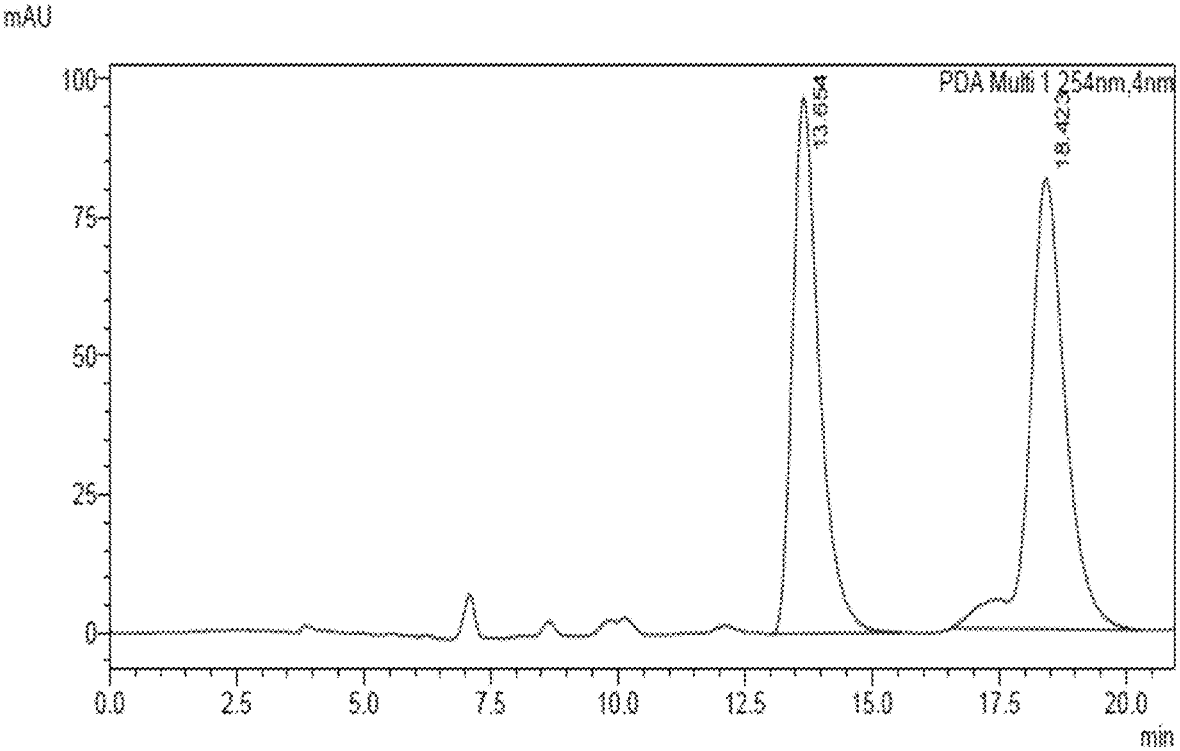
FIG. 5 shows the liquid chromatography of the existing racemic Terbutaline (Homesun Pharmaceutical).

The specific preparation and testing methods of the present invention are conventional methods, such as testing the purity and ee values by conventional liquid chromatography (HPLC+chiral column). With reference to the Example, the present invention will be described in detail.

The preparation method of the present invention may be represented as follows:

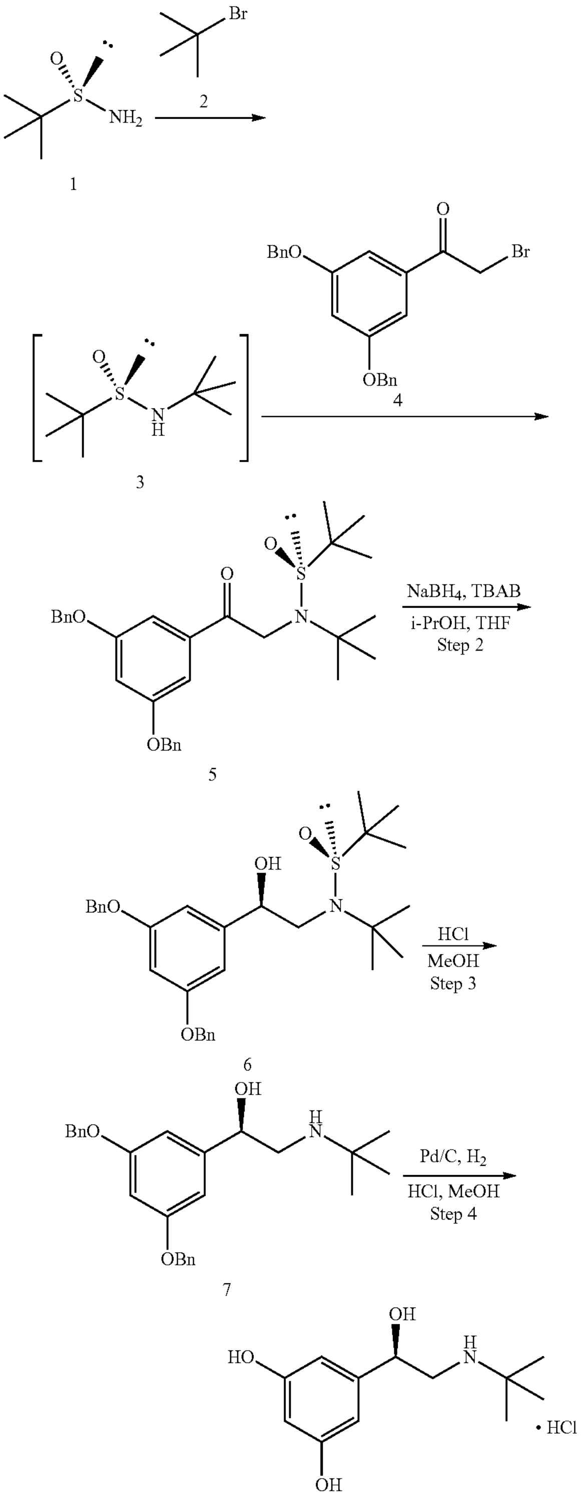

1 2 3 4 5 6 7 8

Example 1

S-(−)-tert-butylsulfinamide (14.8 g, 110 mmol) was dissolved in acetonitrile (300 mL), potassium carbonate (18.0 g, 130 mmol) was added followed by a dropwise addition of tert-butyl bromide (17.8 g, 130 mmol), and then it was heated to 50 °C for reaction for 4 h and then 1-(3,5-bis(benzyloxy)phenyl)-2-bromoethan-1-one (41.1 g, 100 mmol) was added and then reacted at 60 °C for 6 hours. At the end of the reaction, the solids were removed by filtration and then the solvent was removed by distillation under reduced pressure to obtain the compound 5, which was used directly in the next step of the reaction.

The compound 5 obtained above was dissolved in a mixed solvent of THF (200 mL) and isopropanol (200 mL), tetrabutylammonium bromide (3.22 g, 10 mmol) was added, the reaction system was cooled down to 0 °C, and then sodium borohydride (3.02 g, 80 mmol) was added uniformly in three batches within 1.5 hours. After addition, stirring was continued at 0 °C for 1 h. The mixture was quenched by adding aqueous ammonium chloride (50 mL), extracted with ethyl acetate, the extracts were combined, dried over sodium sulfate, distilled under reduced pressure, and the residual solids were crystallized with ethanol (90 mL) to obtain the compound 6 as a white solid of 37.1 g with a yield of 71% after two steps.

The compound 6 (26.1 g, 50 mmol) was dissolved in methanol (150 mL), and concentrated hydrochloric acid (12.5 mL, 37.5 wt %) was added, and the reaction was carried out for 3 hours at 50 °C And after the reaction, the solvent was removed by distillation under reduced pressure, and the residue was added with saturated solution of sodium bicarbonate (80 mL), extracted with ethyl acetate to combine organic layer, dried and distilled under reduced pressure to remove the solvent to obtain the compound 7, which was directly used in the next step of the reaction.

The above obtained compound 7 was dissolved in methanol (200 mL), 10 wt % of palladium-carbon catalyst (2.0 g) was added, and 2 mol/L of hydrogen chloride methanol solution (25 mL) was added dropwise, and then hydrogenated under atmospheric pressure hydrogen for 2 h. Then it was then filtered to remove the palladium-carbon, and the filtrate was distilled under conventional reduced-pressure to remove the solvent, and the residual solids were crystallized with tetrahydrofuran (100 mL) to obtain a total of 11.7 g of R-terbutaline hydrochloride with the two-step yield of 85%, purity of 99.7% and optical rotation of $[\alpha]_D^{20}=-39.2$ (c=1.0 in MeOH).

Example 2

On the basis of the Example 1, potassium carbonate (18.0 g, 130 mmol) was replaced with sodium carbonate (130 mmol), and the rest remained unchanged to obtain the R-terbutaline hydrochloride with a purity of 99.6% and an ee of 99.7%.

On the basis of the Example 1, tetrabutylammonium bromide (3.22 g, 10 mmol) was replaced with tetrabutylammonium chloride (10 mmol) and the rest remained unchanged to obtain the R-terbutaline hydrochloride with a purity of 99.5% and an ee of 99.1%.

On the basis of the Example 1, isopropanol (200 mL) was replaced with ethanol (200 mL) and the rest remained unchanged to obtain the R-terbutaline hydrochloride with a purity of 99.1% and an ee of 99.2%.

Control 1

On the basis of Example 1, tetrabutylammonium bromide was removed and the rest remain unchanged to obtain the compound 6 with the two-step yield of 55%, which was further prepared to obtain the R-terbutaline hydrochloride with an ee of 95.2%.

On the basis of Example 1, the mixture of THF (200 mL) and isopropanol (200 mL) were replaced with isopropanol (400 mL), and the rest remained unchanged to obtain the compound 6 with the two-step yield of 60%, which was further prepared to obtain the R-terbutaline hydrochloride with an ee of 98.8%.

On the basis of Example 1, the sodium borohydride (3.02 g, 80 mmol) was replaced with potassium borohydride (80 mmol), and the rest remained unchanged to obtain the compound 6 with the two-step yield of 59%, which was further prepared to obtain the R-terbutaline hydrochloride with an ee of 98.3%.

Example 3

S-(−)-tert-butylsulfinamide (14.8 g, 110 mmol) was dissolved in acetonitrile (300 mL), potassium carbonate (18.0 g, 130 mmol) was added followed by a dropwise addition of tert-butyl bromide (17.8 g, 130 mmol), and then it was heated to 40 °C for reaction for 3 h and then 1-(3,5-bis(benzyloxy)phenyl)-2-bromoethan-1-one (41.1 g, 100 mmol) was added and then reacted at 60 °C for 6 hours. At the end of the reaction, the solids were removed by filtration and then the solvent was removed by distillation under reduced pressure to obtain the compound 5, which was used directly in the next step of the reaction.

The compound 5 obtained above was dissolved in a mixed solvent of THF (200 mL) and isopropanol (200 mL), tetrabutylammonium bromide (3.22 g, 10 mmol) was added, the reaction system was cooled down to 0 °C, and then sodium borohydride (3.02 g, 80 mmol) was added uniformly in three batches within 1.5 hours. After addition, stirring was continued at 0 °C for 1 h. The mixture was quenched by adding aqueous ammonium chloride (50 mL), extracted with ethyl acetate, the extracts were combined, dried over sodium sulfate, distilled under reduced pressure, and the residual solids were crystallized with ethanol (90 mL) to obtain the compound 6.

The compound 6 (26.1 g, 50 mmol) was dissolved in methanol (150 mL), and concentrated hydrochloric acid (12.5 mL, 37.5 wt %) was added, and the reaction was carried out for 3 hours at 50 °C And after the reaction, the solvent was removed by distillation under reduced pressure, and the residue was added with saturated solution of sodium bicarbonate (80 mL), extracted with ethyl acetate to combine organic layer, dried and distilled under reduced pressure to remove the solvent to obtain the compound 7, which was directly used in the next step of the reaction.

The above obtained compound 7 was dissolved in methanol (200 mL), 10 wt % of palladium-carbon catalyst (2.0 g) was added, and 2 mol/L of hydrogen chloride methanol solution (25 mL) was added dropwise, and then hydrogenated under atmospheric pressure hydrogen for 2 h. Then it was then filtered to remove the palladium-carbon, and the filtrate was distilled under conventional reduced-pressure to remove the solvent, and the residual solids were crystallized with tetrahydrofuran (100 mL) to obtain R-terbutaline hydrochloride.

Example 4

S-(−)-tert-butylsulfinamide (14.8 g, 110 mmol) was dissolved in acetonitrile (300 mL), potassium carbonate (18.0 g, 130 mmol) was added followed by a dropwise addition of tert-butyl bromide (17.8 g, 130 mmol), and then it was heated to 50 °C for reaction for 4 h and then 1-(3,5-bis(benzyloxy)phenyl)-2-bromoethan-1-one (41.1 g, 100 mmol) was added and then reacted at 60 °C for 6 hours. At the end of the reaction, the solids were removed by filtration and then the solvent was removed by distillation under reduced pressure to obtain the compound 5, which was used directly in the next step of the reaction.

The compound 5 obtained above was dissolved in a mixed solvent of THF (200 mL) and isopropanol (200 mL), tetra-butylammonium bromide (3.22 g, 10 mmol) was added, the reaction system was cooled down to 5 °C, and then sodium borohydride (3.02 g, 80 mmol) was added uniformly in two batches within 1 h. After addition, stirring was continued at 0 °C for 1 h. The mixture was quenched by adding aqueous ammonium chloride (50 mL), extracted with ethyl acetate, the extracts were combined, dried over sodium sulfate, distilled under reduced pressure, and the residual solids were crystallized with ethanol (90 mL) to obtain the compound 6.

The compound 6 (26.1 g, 50 mmol) was dissolved in methanol (150 mL), and concentrated hydrochloric acid (12.5 mL, 37.5 wt %) was added, and the reaction was carried out for 3 hours at 50 °C And after the reaction, the solvent was removed by distillation under reduced pressure, and the residue was added with saturated solution of sodium bicarbonate (80 mL), extracted with ethyl acetate to combine organic layer, dried and distilled under reduced pressure to remove the solvent to obtain the compound 7, which was directly used in the next step of the reaction.

The above obtained compound 7 was dissolved in methanol (200 mL), 10 wt % of palladium-carbon catalyst (2.0 g) was added, and 2 mol/L of hydrogen chloride methanol solution (25 mL) was added dropwise, and then hydrogenated under atmospheric pressure hydrogen for 2 h. Then it was then filtered to remove the palladium-carbon, and the filtrate was distilled under conventional reduced-pressure to remove the solvent, and the residual solids were crystallized with tetrahydrofuran (100 mL) to obtain R-terbutaline hydrochloride.

Example 5

S-(−)-tert-butylsulfinamide (14.8 g, 110 mmol) was dissolved in acetonitrile (300 mL), potassium carbonate (18.0 g, 130 mmol) was added followed by a dropwise addition of tert-butyl bromide (17.8 g, 130 mmol), and then it was heated to 50 °C for reaction for 4 h and then 1-(3,5-bis (benzyloxy)phenyl)-2-bromoethan-1-one (41.1 g, 100 mmol) was added and then reacted at 60 °C for 6 hours. At the end of the reaction, the solids were removed by filtration and then the solvent was removed by distillation under reduced pressure to obtain the compound 5, which was used directly in the next step of the reaction.

The compound 5 obtained above was dissolved in a mixed solvent of THF (200 mL) and isopropanol (200 mL), tetra-butylammonium bromide (3.22 g, 10 mmol) was added, the reaction system was cooled down to 0 °C, and then sodium borohydride (3.02 g, 80 mmol) was added uniformly in three batches within 1.5 hours. After addition, stirring was continued at 0 °C for 1 h. The mixture was quenched by adding aqueous ammonium chloride (50 mL), extracted with ethyl acetate, the extracts were combined, dried over sodium sulfate, distilled under reduced pressure, and the residual solids were crystallized with ethanol (90 mL) to obtain the compound 6.

The compound 6 (26.1 g, 50 mmol) was dissolved in methanol (150 mL), and concentrated hydrochloric acid (12.5 mL, 37.5 wt %) was added, and the reaction was carried out for 4 hours at 50 °C And after the reaction, the solvent was removed by distillation under reduced pressure, and the residue was added with saturated solution of sodium bicarbonate (80 mL), extracted with ethyl acetate to combine organic layer, dried and distilled under reduced pressure to remove the solvent to obtain the compound 7, which was directly used in the next step of the reaction.

The above obtained compound 7 was dissolved in methanol (200 mL), 10 wt % of palladium-carbon catalyst (2.0 g) was added, and 2 mol/L of hydrogen chloride methanol solution (25 mL) was added dropwise, and then hydrogenated under atmospheric pressure hydrogen for 2 h. Then it was then filtered to remove the palladium-carbon, and the filtrate was distilled under conventional reduced-pressure to remove the solvent, and the residual solids were crystallized with tetrahydrofuran (100 mL) to obtain R-terbutaline hydrochloride.

Example 6

S-(−)-tert-butylsulfinamide (14.8 g, 110 mmol) was dissolved in acetonitrile (300 mL), potassium carbonate (18.0 g, 130 mmol) was added followed by a dropwise addition of tert-butyl bromide (17.8 g, 130 mmol), and then it was heated to 50 °C for reaction for 4 h and then 1-(3,5-bis (benzyloxy)phenyl)-2-bromoethan-1-one (41.1 g, 100 mmol) was added and then reacted at 60 °C for 6 hours. At the end of the reaction, the solids were removed by filtration and then the solvent was removed by distillation under reduced pressure to obtain the compound 5, which was used directly in the next step of the reaction.

The compound 5 obtained above was dissolved in a mixed solvent of THF (200 mL) and isopropanol (200 mL), tetra-butylammonium bromide (3.22 g, 10 mmol) was added, the reaction system was cooled down to 0 °C, and then sodium borohydride (3.02 g, 80 mmol) was added uniformly in three batches within 1.5 hours. After addition, stirring was continued at 0 °C for 1 h. The mixture was quenched by adding aqueous ammonium chloride (50 mL), extracted with ethyl acetate, the extracts were combined, dried over sodium sulfate, distilled under reduced pressure, and the residual solids were crystallized with ethanol (90 mL) to obtain the compound.

The compound 6 (26.1 g, 50 mmol) was dissolved in methanol (150 mL), and concentrated hydrochloric acid (12.5 mL, 37.5 wt %) was added, and the reaction was carried out for 3 hours at 50 °C And after the reaction, the solvent was removed by distillation under reduced pressure, and the residue was added with saturated solution of sodium bicarbonate (80 mL), extracted with ethyl acetate to combine organic layer, dried and distilled under reduced pressure to remove the solvent to obtain the compound 7, which was directly used in the next step of the reaction.

The above obtained compound 7 was dissolved in methanol (200 mL), 10 wt % of palladium-carbon catalyst (2.0 g) was added, and 2 mol/L of hydrogen chloride methanol solution (25 mL) was added dropwise, and then hydrogenated under atmospheric pressure hydrogen for 2.5 h. Then it was then filtered to remove the palladium-carbon, and the filtrate was distilled under conventional reduced-pressure to remove the solvent, and the residual solids were crystallized with tetrahydrofuran (100 mL) to obtain R-terbutaline hydrochloride.

The method provided by the present invention is to use cheap and readily available chiral tert butyl sulfonamide as a chiral auxiliary, and reduce it to the desired chiral secondary alcohol by controlling the asymmetric reduction of ketone, and the chiral auxiliary can be removed under simple acidic conditions.

The invention claimed is:

1. A method for preparing R-terbutaline using a chiral auxiliary, comprising hydrogenating a compound 7 in an alcohol solvent in the presence of a palladium catalyst and hydrochloric acid to obtain R-terbutaline;

the chemical structural formula of the compound 7 is as follows:

7

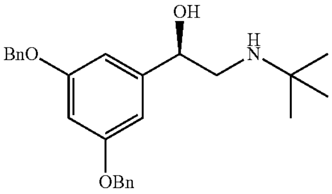

, the chemical structural formula of R-terbutaline is as follows:

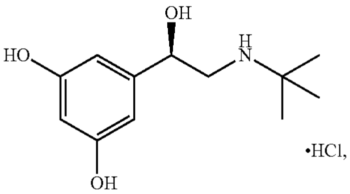

•HCl, wherein S-(−)-tert-butylsulfinamide is used as starting material to react with tert-butyl bromide and 1-(3,5-bis(benzyloxy)phenyl)-2-bromoethan-1-one 4 sequentially to obtain a compound 5; compound 5 undergoes a reduction reaction to obtain a compound 6; the compound 6 is de-protected from tert-butylsulfonyl group to obtain the compound 7;

the chemical structural formula of compound 5 is as follows:

5

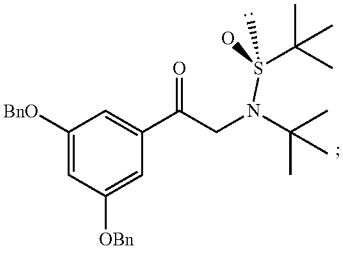

;

and the chemical structural formula of compound 6 is as follows:

6

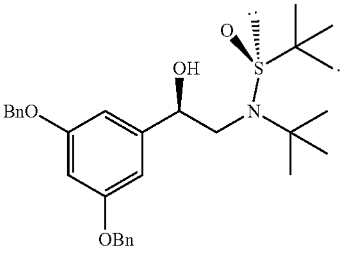

.

2. The method for preparing R-terbutaline using a chiral auxiliary according to claim 1, wherein S-(−)-tert-butylsulfinamide is dissolved in an organic solvent, a base is added, then tert-butyl bromide is added dropwise, and the reaction is carried out at 0-60 °C for 2-5 hours, followed by the addition of 1-(3,5-bis(benzyloxy)phenyl)-2-bromoethan-1-one 4, and the reaction is continued at 30-80 °C for 2-8 hours to obtain the compound 5.

3. The method for preparing R-terbutaline using a chiral auxiliary according to claim 1, wherein the compound 5 is dissolved in a solvent, a quaternary ammonium salt is added, then sodium borohydride is added at 0-10 °C, to obtain the compound 6.

4. The method for preparing R-terbutaline using a chiral auxiliary according to claim 1, wherein compound 6 is dissolved in methanol, and concentrated hydrochloric acid is added, and the reaction is carried out for 2~5 hours at 0~60 °C to obtain the compound 7.

5. The method for preparing R-terbutaline using a chiral auxiliary according to claim 1, wherein the palladium catalyst is an inorganic palladium catalyst; and the alcohol solvent is methanol.

6. The method for preparing R-terbutaline using a chiral auxiliary according to claim 5, wherein the palladium catalyst is a palladium-carbon catalyst; and the alcohol solvent is methanol.

7. The method for preparing R-terbutaline using a chiral auxiliary according to claim 1, wherein the compound 7 is dissolved in the alcohol solvent, the palladium catalyst is added, hydrochloric acid is dropped dropwise, and hydrogenolysis is carried out in atmospheric hydrogen gas for 1-3 hours to obtain R-terbutaline.

N

* * * * *